US00PP25863P3

(12) United States Plant Patent

Slaughter et al.

(10) Patent No.: US PP25,863 P3

(45) Date of Patent: Sep. 8, 2015

(54) NECTARINE TREE NAME 'BURNECTTHIRTY'

(50) Latin Name: ***Prunus persica* (subspecies *nucipersica*)**
Varietal Denomination: Burnectthirty

(71) Applicants: John K. Slaughter, Fresno, CA (US); Timothy J. Gerdts, Kingsburg, CA (US)

(72) Inventors: John K. Slaughter, Fresno, CA (US); Timothy J. Gerdts, Kingsburg, CA (US)

(73) Assignee: THE BURCHELL NURSERY, INC., Oakdale, CA (US)

( * ) Notice: Subject to any disclaimer, the term of this patent is extended or adjusted under 35 U.S.C. 154(b) by 90 days.

(21) Appl. No.: 13/998,824

(22) Filed: Dec. 11, 2013

(65) Prior Publication Data

US 2015/0163975 P1 Jun. 11, 2015

(51) Int. Cl.
*A01H 5/08* (2006.01)

(52) U.S. Cl.
USPC ..... Plt./190

(58) Field of Classification Search
USPC ..... Plt./187, 190
See application file for complete search history.

*Primary Examiner* — Susan McCormick Ewoldt

(74) *Attorney, Agent, or Firm* — Paine Hamblen, LLP

(57) ABSTRACT

A new and distinct variety of nectarine tree (*Prunus persica* sub species *nuciperisica*), and which is denominated varietally as 'Burnectthirty', and which further produces an attractively colored yellow-fleshed, non-melting, acidic clingstone nectarine, which is mature for harvesting and shipment approximately May 18 to May 25 under ecological conditions prevailing in the San Joaquin Valley of central California.

1 Drawing Sheet

Botanical designation: The present invention relates to a new, novel and distinct variety of nectarine tree, *Prunus persica* (subspecies *nucipersica*).

Variety denomination: 'Burnectthirty.'

BACKGROUND OF THE NEW VARIETY

The present variety of nectarine tree resulted from an ongoing program of fruit and nut tree breeding. The purpose of this program is to improve the commercial quality of available deciduous fruit and nut varieties, and rootstocks, by creating and releasing promising selections of *prunus, malus, punica* and *regia* species. To this end we make both controlled and hybrid cross pollinations each year in order to produce seedling populations from which improved progenies are evaluated and selected.

The seedling 'Burnectthirty' was originated by us from a population of seedlings grown in our experimental orchards which are located near Fowler, Calif. The seedlings, grown on their own roots, were the result of a controlled cross made in February of 2007, of the yellow-fleshed nectarine tree, 'Burnectwentytwo' (U.S. Pat. No. 21,724), which was the seed parent; and the white-fleshed nectarine tree, 'Burnectwentythree' (U.S. Pat. No. 17,890) and which was used as the pollen parent. One seedling, identified as Q56.074, and which is the present variety, exhibited especially desirable characteristics, and was marked for subsequent observation. After the 2009 fruiting season, the new, present variety, was selected for advanced evaluation, and repropagation.

ASEXUAL REPRODUCTION

Asexual reproduction of the new and distinct variety of nectarine tree was accomplished by budding the new nectarine tree to 'Nemaguard' Rootstock (non-patented). This was performed by us in our experimental orchard which is located near Fowler, Calif. Subsequent evaluations have shown those asexual reproductions run true to the original tree. All characteristics of the original tree, and its fruit, were established, and appear to be transmitted through succeeding asexual propagations. We have observed fruit for the past 4 successive years from approximately 15 previously propagated trees.

SUMMARY OF THE VARIETY

'Burnectthirty' is a new and distinct variety of nectarine tree, which produces fruit that are considered of large size, and which further displays vigorous growth. This new nectarine tree variety is also a regular and productive bearer of relatively large, firm, acidic, yellow fleshed, melting, clingstone fruit which have good flavor and eating quality. The tree of the present variety displays a medium chilling requirement of approximately 350 hours. Still further, the present tree also produces relatively uniformly sized fruit throughout the tree. Additionally, the fruit produced by the present tree displays a very high degree of red skin coloration, a firm flesh, and further appears to have good handling and shipping qualities. The 'Burnectthirty' Nectarine tree also bears fruit which are ripe for commercial harvesting, and shipment, on approximately May 18 to May 25 under the ecological conditions prevailing in the San Joaquin Valley of central California. In relative comparison to the seed parent, the new variety, 'Burnectthirty', ripens 7-10 days earlier. In relative comparison to the pollen parent, the 'Burnectwentythree' nectarine tree, the current new variety ripens 20 days earlier. In addition to the aforementioned distinctions, the current variety produces a yellow-fleshed nectarine which has a globose fruit form which is in contrast to the pollen parent, the 'Burnectwentythree' and which produces a white-fleshed and saucer shaped fruit. In relative comparison to the nectarine tree, 'May Bright' (U.S. Pat. No. 21,928), and which is the most similar commercial variety known to the breeders at this time, the new present variety is both larger in size and ripens 5 days earlier where grown under similar growing conditions.

BRIEF DESCRIPTION OF THE DRAWINGS

The accompanying drawing, which is provided, is a color photograph of the new variety of nectarine tree.

The photograph depicts two whole mature fruit displaying both apical and basal aspects, and one mature fruit which is dissected substantially in the equatorial plane, and is further viewed from the apical perspective. This photograph reveals the flesh and the stone characteristics of the new variety. The external coloration of the fruit, as shown in the photograph, is sufficiently matured for harvesting and shipment. Additionally, the photograph displays a sample vegetative shoot bearing typical leaves; a sample piece of bark; and a typical stone, with the fleshed removed.

The colors in this photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society, fourth Edition, 2001) and the descriptions as provided, hereinafter.

NOT A COMMERCIAL WARRANTY

The following detailed description has been prepared to solely comply with the provisions of 35 U.S.C. § 112, and does not constitute a commercial warranty (either expressed or implied) that the present variety will in the future display all of the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of nectarine tree, the following has been observed during the fourth fruiting season under the ecological conditions prevailing at our test orchards which are located near the town of Fowler, county of Fresno, state of California. All major color code designations are by reference to The R.H.S. Colour Chart (Fourth Edition), and which is provided by The Royal Horticultural Society of Great Britain. Common color names are also occasionally used.

TREE

Size:

*Generally*.—Considered medium-large as compared to other common commercial nectarine cultivars ripening in the early season of maturity.

Tree height: Approximately 305.0 cm.

Canopy width: Approximately 300.0 cm.

Vigor: Considered moderately vigorous. The present variety grew from about 185.0 cm to 195.0 cm in height during the first growing season. The new nectarine tree variety was pruned to a height of approximately 175.0 cm during the first dormant season, and primary scaffolds were then selected for the desired and resulting tree structure.

Productivity: Productive. Fruit set varies from 4.0 to several times more than the desired crop load. The resulting fruit set is determined, at least in part, by thinning of the tree to develop the remaining fruit into the desired market sized fruit. The number of the fruit set varies with prevailing climatic conditions, and the cultural practices employed.

Fruit bearing: Regular. Fruit set has been heavy, and significant thinning was necessary during the past 4 years on the propagated trees which were observed.

Tree form: Extremely upright, and pruned to a vase shape.

Tree density: Considered medium dense. It has been discovered that pruning the branches from the center of the tree to obtain a resulting vase shape allows for proper air movement in the tree, and appropriate amounts of sunlight to be received so as to enhance the resulting fruit color, and renewal of fruiting wood throughout the canopy of the tree.

Hardiness: The present tree was grown and evaluated in USDA Hardiness zone 9.

Winter chilling requirements: The new tree requires approximately 350 hours of chilling below 7.0 degrees C. The variety also appears to be hardy under typical Central San Joaquin Valley climatic conditions.

TRUNK

Diameter: Approximately 15.0 cm in diameter when measured at a distance of approximately 15.24 cm above the soil level, when this was measured at the end of the fourth growing season.

Bark texture: Considered moderately rough, with numerous folds of papery scarfskin being present.

Lenticels: Numerous flat, oval lenticels are present. The lenticels range in size from approximately 5.0 to about 7.0 millimeters in width, and from about 1.0 to about 2.0 millimeters in height. It should be noted that as the cork (bark) of the trees mature, the lenticels become less apparent and less abundant.

Lenticel color: Considered an Orange Brown, (RHS Greyed-Orange Group N167 A).

Bark coloration: Variable, but it is generally considered to be gray-brown, (RHS Greyed-Orange Group 174 A).

BRANCHES

Size: Considered medium for the variety.

Diameter: Average as compared to other nectarine tree varieties. The branches have a diameter of about 7.5 centimeters when measured during the fourth year after grafting.

Surface texture: Average, and appearing furrowed on wood which is several years old.

Crotch angles: Primary branches are considered variable, and quite acute when compared to the general growth habits that are displayed by commercial varieties. The growth habit is not currently considered a pillar/columnar form but is, rather, substantially upright. Limb angles are approximately 60 to about 64 degrees from the horizontal axis. This particular characteristic is relatively distinctive of the variety but can be influenced by ecological and seasonal influences, and other cultural practices, however.

Current season shoots:

*Surface texture*.—Substantially glabrous.

Internode length: Approximately 2.4 to about 3.0 cm. This tree characteristic is highly dependent upon plant nutrition, soil quality, pruning and tree care and therefore is not distinctive of the present variety.

Color of mature branches: Medium brown, (RHS Greyed-Orange 165B).

Current seasons shoots:

*Color.*—Light green, (RHS Green Group 137C). The color of the new shoot tips is considered a bright and shiny green (RHS Green Group 136B).

LEAVES

Size: Considered medium for the species. Leaf measurements have been taken from vigorous, upright, current-season growth, at approximately the mid-shoot.

Leaf length: Approximately 146.0 to about 155.0 millimeters.

Leaf width: Approximately 33.0 to about 38.0 millimeters.

Leaf base shape: Slightly oblique relative to the leaf longitudinal axis.

Leaf form: Lanceolate.

Leaf tip form: Considered acutus.

Leaf color:

*Upper surface.*—Dark green, (approximately RHS Green Group 131B).

Leaf texture: Glabrous.

Leaf color:

*Lower surface.*—Medium green, (RHS Green Group 131C).

Leaf venation: Pinnately veined.

Mid-vein:

*Color.*—Light yellow green, (RHS Green Group 139B).

Leaf margins: Slightly undulating.

*Form.*—Considered crenate.

*Uniformity.*—Considered generally uniform.

Leaf petioles:

*Size.*—Considered medium for the species.

*Length.*—About 7.5 to about 9.0 mm.

*Diameter.*—About 1.5 to about 2.0 mm.

*Color.*—Pale green, (RHS Yellow-Green Group 139C).

Leaf glands:

*Size.*—About 1.0 mm in height, and about 1.0 mm in width.

*Number.*—Generally one per side, occasionally two per side.

*Type.*—Reniform.

*Color.*—Orange brown, (RHS Greyed-Brown Group 199A).

Leaf stipules:

*Size.*—Medium for the variety.

*Length.*—Approximately 6.0 mm.

*Width.*—Approximately 1.2 mm.

*Number.*—Typically 2 per leaf bud, and up to 6 per shoot tip.

*Form.*—Lanceolate in form, and having a serrated margin.

*Color.*—Green, (RHS Green Group 141 B) when young, but graduating to a brown color, (RHS Greyed-Orange group 165 A) with advancing senescence. The stipules are considered to be early deciduous.

FLOWER BUDS

Flower buds:

*Generally.*—The floral buds, depending upon the stage of development, are approximately 12.0 millimeters wide; and about 17.0 millimeters long; conic in form; and slightly appressed relative to the bearing shoot.

Flower buds:

*Color.*—The bud scales are reddish-brown, (approximately RHS Greyed Purple Group 183 A). The buds are considered hardy under typical central San Joaquin Valley climatic conditions.

Hardiness: No winter injury has been noted during the last several years of evaluation in the central San Joaquin Valley. The current variety has not been intentionally subjected to drought or heat stress, and therefore this information is not available. The current variety is considered to have a lower chill requirement in the region where it currently is grown. It is possible for the new variety to experience frost damage on either of the flowers or small fruit due the early initiation of the blooming period, and the subsequent exposure of the flowers or small fruit to the damaging effects of the low temperatures during the late winter months after the bloom.

FLOWERS

Date of first bloom: Feb. 12, 2013.

Blooming time: Considered early season in relative comparison to other commercial nectarine cultivars grown in the central San Joaquin Valley.

Date of full bloom: This was observed on Feb. 21, 2013. The date of bloom varies slightly with the prevailing climatic conditions, and cultural practices.

Duration of bloom: Approximately 10 days. This characteristic varies slightly with climatic conditions.

Flower class: Perfect, complete and perigynous.

Flower type: The variety is considered to have a showy type flower.

Flower size: The flower diameter at full bloom is approximately 45.0 to about 48.0 millimeters.

Bloom quantity: Considered very abundant.

Flower bud frequency: Normally 2 flower buds appear per node. Rarely more than 3 buds per node are observed.

Petal size:

*Generally.*—Considered very large for the species.

*Length.*—Approximately 20.0 to about 26.0 millimeters.

*Width.*—Approximately 15.0 to about 20.0 millimeters.

Petal form: Rotund to slightly ovate.

Petal count: Generally 5 large petals are observed. In addition to those previously described, there are often extra, smaller, underdeveloped flower petals present particularly on younger trees.

Petal texture: Glabrous.

Petal color: Light pink, (RHS Red-Purple Group 65 B) to a medium pink, (RHS Red-Purple Group 65 A).

Fragrance: Slight.

Petal claw:

*Form.*—The claw is considered truncate in shape, and has a large size when compared to other varieties.

*Length.*—Approximately 13.5 to about 15.0 millimeters.

*Width.*—Approximately 12.0 to about 14.0 millimeters.

Petal margins: Generally considered variable, from nearly smooth, to moderately undulate.

Petal apex:

*Generally.*—The petal apices generally appear entire with a small apical groove.

*Size.*—Approximately 1.5 mm in length, and approximately 1.0 mm in width.

Flower pedicel:

*Length.*—Considered medium-long, and having an average length of approximately 7.5 to about 8.0 millimeters.

*Diameter.*—Considered average, approximately 2.0 millimeters.

*Color.*—A pale green, (RHS Greyed-Green Group 194 B).

Floral nectaries:

*Color.*—A reddish brown, (RHS Greyed-Red Group 178 B).

Calyx:

*Surface texture.*—Generally glabrous.

*Color.*—A dull red, (approximately RHS Greyed-Purple Group 184 B).

Sepals:

*Surface texture.*—The surface has a short, fine, pubescent texture.

*Number.*—Generally always five.

*Size.*—Average.

*Sepal length.*—Approximately 3.5 mm to 5.0 mm.

*Sepal width.*—Approximately 3.0 mm to 4.5 mm.

*Sepal shape.*—A single entire deltoid shaped lobe is observed.

*Sepal margin.*—Smooth, entire.

*Sepal color.*—A dark reddish purple, (approximately RHS Greyed-Purple Group 183D).

Anthers:

*Generally.*—Large in size.

*Color.*—Red to reddish purple, (approximately RHS Greyed-Purple Group 187C) prior to dehiscence.

Pollen production: Pollen is abundant, and has a yellow color, (approximately RHS Yellow Group 13 A).

Fertility: Self fertile.

Filaments:

*Size.*—Variable in length, approximately 15.0 to about 19.0 millimeters in length.

*Color.*—Considered a pale pink, (RHS White Group 155 B).

Pistil:

*Number.*—Normally 1, very rarely 2.

*Generally.*—Large in size.

*Length.*—Approximately 18.0 to about 22.0 millimeters including the ovary.

*Color.*—Considered a very pale green, (approximately RHS Yellow-Green Group 145 C).

*Surface texture.*—The variety has a long glabrous pistil.

FRUIT

Maturity when described: Firm ripe condition (shipping ripe).

*Date of first picking.*—May 18, 2013.

*Date of last picking.*—May 25, 2013. The date of harvest varies slightly with the prevailing climatic conditions.

Size:

*Generally.*—Considered large, and uniform.

Average cheek diameter: Approximately 68.0 to about 72.0 millimeters.

Average axial diameter: Approximately 69.0 to about 75.0 millimeters.

Typical weight: Approximately 250.0 grams. This characteristic is highly dependent upon currently employed cultural practices, and therefore is not particularly distinctive of this new variety.

Fruit form:

*Generally.*—Rounded to slightly oblate. The fruit is generally quite uniform in symmetry.

Fruit suture: Relatively full. No apparent callousing or stitching exists along the suture line.

Suture:

*Color.*—The background color appears to be an orange yellow, (approximately RHS Yellow-Orange Group 16 B), with occasional red coloration appearing (approximately RHS Red Group 46 A).

Ventral surface:

*Form.*—Full.

Apex: Rounded.

Base shape: Generally Retuse.

Stem cavity shape: Rounded, centered, and relatively shallow in depth. The average depth of the stem cavity is about 5.0 mm. The average width of the stem cavity is about 15.0 mm.

Fruit skin:

*Thickness.*—Considered medium in thickness, and tenacious to the flesh.

*Texture.*—Glabrous.

*Taste.*—Slight astringency is detected.

*Tendency to crack.*—Cracking has not been observed. Russeting has not been observed to date.

Fruit skin color:

*Blush color.*—The blush color is variable from a medium red, (approximately RHS Red Group 44 A) to a dark red, (approximately RHS Red Group 46A). The blush color ranges from about 85% to about 95% of the fruit surface depending upon the sunlight exposure, and prevailing climate, canopy development and growing conditions.

Ground color: Generally a deep yellow, (approximately RHS Yellow-Orange Group 16B).

Fruit stem: Moderate in length, approximately 8.0 to about 10.0 millimeters.

*Diameter.*—Approximately 2.0 to about 3.0 millimeters.

*Color.*—Light tan, (approximately RHS Greyed-Orange Group 164 C).

Flesh:

*Ripening.*—Considered generally even.

*Texture.*—Firm, and dense. Considered non-melting.

*Fibers.*—Few, small, and tender ones are apparent.

*Aroma.*—Slight.

*Eating quality.*—Considered good.

*Flavor.*—Considered sweet and acidic. The flavor is considered pleasant.

*Acidity.*—Considered an acidic fruit. Titratable acidity of about 0.9 was detected.

*Juice production.*—Abundant.

*Brix.*—About 13.0 degrees. This characteristic varies slightly with the number of fruit per tree; the prevailing cultural practices; and the surrounding climatic and ecological conditions.

*Flesh color.*—Yellow, (approximately RHS Yellow-Orange Group 17 D).

STONE

Type: Clingstone.

Size: Considered medium large for the variety. The stone size varies with the resulting crop load, and tree vigor, and therefore is not considered a distinguishing characteristic of this new variety.

Length: Average, about 24.0 to about 28.0 millimeters.
Width: Average, about 20.0 to about 24.0 millimeters.
Diameter: Average, about 18.0 to about 23.0 millimeters.
Stone form: Obovoid.
Stone base: The stone is relatively uniform in its margin relative to the stone's vertical axis.
Apex:
*Shape*.—The stone apex is relatively uneven with an acute tip.
Stone surface:
*Surface texture*.—Substantial pitting is evident, in general, from the base past the equatorial plane, and proceeding apically until the peripheral grooves. Grooving is usually observed along the pit margin near the tip and on the ventral side.
*Ridges*.—The surface texture is generally rounded.
*Ventral edge*.—Width — Considered medium, and having a dimension of approximately 2.7 to about 3.0 millimeters when measured at the mid-suture.
*Dorsal edge*.—Shape. — Full, heavily grooved, and having somewhat irregular edges especially toward the apex.
Stone color: The color of the dry stone is a tan (Greyed-Orange Group approximately RHS 174 D). The stone as seen in the photo is freshly exposed and the color can alter because of the effects of oxidation as drying of the stone proceeds.
Tendency to split: Rarely, splits have been noted.
Kernel:
*Generally*.—The kernel, when the fruit is picking ripe, is not completely mature when compared to kernels of fruit varieties with a greater development period.
*Length*.—Approximately 15.0 millimeters.
*Width*.—Approximately 10.0 millimeters.
*Thickness*.—Approximately 3.5 mm.
*Form*.—Considered ovoid.
*Pellicle*.—Pubescent.
*Color*.—Considered to be a pale tan (Greyed-Yellow Group 160 C).
Use: The subject variety 'Burnectthirty' is considered to be a Nectarine tree which matures early in the season, and which produces fruit, which are considered firm, attractively colored, flavorful, and which are useful for both local and long distance shipping.
Keeping quality: Excellent. Fruit has stored well for 28 days after harvest at 1.0 degree Celsius.
Shipping quality: Good. The fruit of the new nectarine tree variety showed minimal bruising of the flesh, or skin damage, after being subjected to normal harvest and packing procedures.
Resistance to insects and disease: No particular susceptibilities were noted. The present variety has not been tested to expose or detect any susceptibilities or resistances to any known plant and/or fruit diseases.
Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by plant Letters Patent is:

1. A new distinct variety of nectarine tree, substantially as illustrated and described, and which is characterized principally as to novelty by producing an attractively colored, yellow-fleshed, non-melting, and acidic clingstone nectarine which is mature for harvesting and shipment approximately May 18 to May 25 under the ecological conditions prevailing in the San Joaquin Valley of central California.

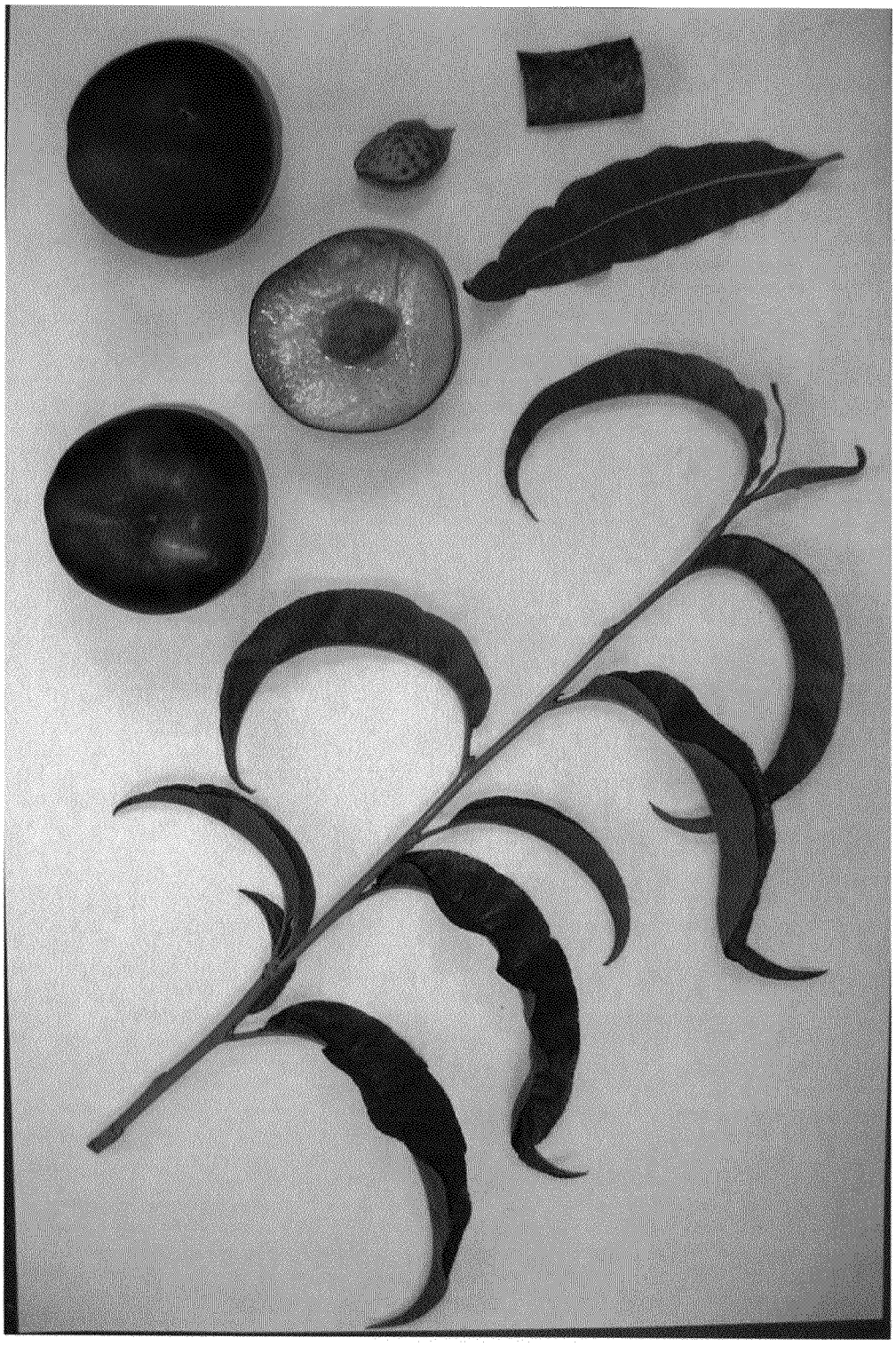

* * * * *